United States Patent [19]
Duan et al.

[11] Patent Number: 6,042,811
[45] Date of Patent: Mar. 28, 2000

[54] AEROSOL FORMULATION CONTAINING A DIOL-DIACID DERIVED DISPERSING AID

[75] Inventors: Daniel C. Duan, St. Paul; James S. Stefely, Woodbury; David W. Schultz, Pine Springs; Chester L. Leach, Lake Elmo, all of Minn.

[73] Assignee: 3M Innovative Properties Company, St. Paul, Minn.

[21] Appl. No.: 08/214,763

[22] Filed: Mar. 16, 1994

Related U.S. Application Data

[63] Continuation-in-part of application No. 08/032,605, Mar. 17, 1993, abandoned.

[51] Int. Cl.$^7$ ................................................ A61K 9/12
[52] U.S. Cl. ................................................ 424/45; 424/46
[58] Field of Search ................................ 424/45, 78.17, 424/46; 528/272, 300, 301, 302

[56] References Cited

U.S. PATENT DOCUMENTS

| | | | |
|---|---|---|---|
| 2,362,511 | 11/1944 | Teeters | 260/78 |
| 2,733,252 | 1/1956 | Thompson et al. | 260/410.9 |
| 2,789,992 | 4/1957 | Thompson et al. | 260/410.9 |
| 3,098,795 | 7/1963 | Kreps | 167/90 |
| 3,728,447 | 4/1973 | Osipow et al. | 424/70 |
| 3,933,825 | 1/1976 | Fiscella et al. | 260/268 R |
| 4,029,606 | 6/1977 | Isa et al. | 252/529 |
| 4,846,991 | 7/1989 | Suzue et al. | 252/89.1 |
| 5,008,028 | 4/1991 | Jolley et al. | 252/68 |
| 5,126,123 | 6/1992 | Johnson | 424/45 |
| 5,225,183 | 7/1993 | Purewal et al. | 424/45 |
| 5,658,549 | 8/1997 | Akehurst et al. | 424/45 |

FOREIGN PATENT DOCUMENTS

| | | |
|---|---|---|
| 666406 A5 | 7/1988 | China . |
| 534731 A1 | 3/1993 | European Pat. Off. . |
| 0551748 | 7/1993 | European Pat. Off. . |
| 91/04011 | 4/1991 | WIPO . |
| 91/14422 | 10/1991 | WIPO . |
| 92/00061 | 1/1992 | WIPO . |
| 92/00062 | 1/1992 | WIPO . |

OTHER PUBLICATIONS

*Polymer Preprints,*Japan (English Edition), vol. 41, No. 5–11, p. 1681.
JP 04169554 A (Derwent Abstract).
JP 04198394 A (Derwent Abstract).
Chemical Abstracts 117(14):134330a (Fujii, Mar. 1992).
Chemical Abstracts 117(14):134337h (Nakahara, Mar. 1992).
Chemical Abstracts 117(14):134340d (Tanaka. Mar. 1992).
Chemical Abstracts 117(24):237045r (Nakahara, May 1992).
Chemical Abstracts 117(24):237046s (Nakahara, May 1992).
Chemical Abstracts 117(26):254711x (Fujii, Jun. 1992).
Chemical Abstracts 118(4):2870q (Fujii, Jun. 1992).
Chemical Abstracts 118(8):62799f (Lache, 1991).
Chemical Abstracts 118(12):106175f (Nakahara, Nov. 1992).

*Primary Examiner*—Raj Bawa
*Attorney, Agent, or Firm*—Ted K. Ringsred; MarySusan Howard; Robert W. Sprague

[57] ABSTRACT

A medicinal aerosol formulation containing a particulate drug and a diol/diacid condensate as a dispersing aid.

24 Claims, No Drawings

AEROSOL FORMULATION CONTAINING A DIOL-DIACID DERIVED DISPERSING AID

CROSS-REFERENCE TO RELATED APPLICATION

This application is a continuation-in-part of U.S. Application 08/032,605, filed 17 Mar. 1993, now abandoned.

BACKGROUND OF THE INVENTION

1. Field of the Invention

This invention relates to aerosol drug formulations. This invention also relates to dispersing aids for use in aerosol drug formulations. In another aspect this invention relates to aerosol formulations comprising hydrofluorocarbon propellants.

2. Description of the Related Art

Delivery of drugs to the lung by way of inhalation is an important means of treating a variety of conditions, including such common conditions as bronchial asthma and chronic obstructive pulmonary disease. Steroids, β-2 agonists, and anti-cholinergic agents are among the drugs that are administered to the lung for such purposes. Such drugs are commonly administered to the lung in the form of an aerosol of particles of respirable size (less than about 10 µm in diameter). In order to assure proper particle size in the aerosol, particles can be prepared in respirable size and then incorporated into a suspension formulation containing a propellant. Alternatively, formulations can be prepared in solution form in order to avoid the concern for proper size of particles in the formulation. Solution formulations nevertheless must be dispensed in a manner that produces particles or droplets of respirable size.

Once prepared, an aerosol formulation is filled into an aerosol canister equipped with a metered dose valve. In the hands of a patient the formulation is dispensed via an actuator adapted to direct the dose from the valve to the patient.

It is important that an aerosol formulation be stable such that the dose discharged from the metered dose valve is reproducible. Rapid creaming, settling, or flocculation after agitation are common sources of dose irreproducibility in suspension formulations. Sticking of the valve also can cause dose irreproducibility. In order to overcome these problems, aerosol formulations often contain surfactants, which serve as suspending aids to stabilize the suspension for a time sufficient to allow for reproducible dosing. Certain surfactants also function as lubricants to lubricate the valve to assure smooth actuation. Myriad materials are known and disclosed for use as dispersing aids in aerosol formulations. Suitability of materials, however, is dependent on the particular drug and the propellant or class of propellant used in the formulation.

It is sometimes difficult to dissolve sufficient quantities of conventional surfactants in hydrofluorocarbon (HFC) propellants such as HFC-134a and HFC-227. Cosolvents have been used to overcome this problem. An alternative approach that avoids the use of cosolvents involves materials that are soluble in hydrofluorocarbon propellants and are said to be effective surfactants or dispersing aids in an aerosol formulation. Among such materials are certain fluorinated surfactants and certain polyethoxy surfactants.

As the materials used in medicinal aerosol formulations are taken into the lungs it is desirable that they be suitably eliminated, metabolized, or non-toxic.

SUMMARY OF THE INVENTION

This invention provides a medicinal aerosol formulation, comprising:

(i) a dispersing aid comprising a compound comprising a chain of diol/diacid condensate units;

(ii) a propellant; and (iii) a therapeutically effective amount of a particulate drug;

wherein the formulation is substantially readily redispersible and when redispersed does not flocculate, settle, or cream so quickly as to prevent reproducible dosing of the drug.

In another embodiment the dispersing aid comprises a compound comprising a chain comprising a plurality of units of the general formula $$-\!\!\left(\!\!\begin{array}{c}O\\\|\\C\end{array}\!\!-R_1\!-\!\!\begin{array}{c}O\\\|\\C\end{array}\!\!-O\!-\!R_2\!-\!O\!\right)\!\!-$$

wherein each $R_1$ is an independently selected organic moiety that links the carbonyl groups and each $R_2$ is an independently selected organic moiety that links the oxy groups.

DETAILED DESCRIPTION OF THE INVENTION

This invention involves suspension aerosol formulations comprising a dispersing aid. The dispersing aid comprises one or more compounds. The compound or compounds in the dispersing aid comprise at least one chain, which can be linear, branched, or cyclic.

The chain comprises diol/diacid condensate units. As the terminology is used herein, a "diol/diacid condensate unit" need not be prepared by the condensation of a diol with a diacid; rather this terminology is used to designate chains having a structure that could in principle be obtained by a condensation reaction of a diacid with a diol. Likewise, reference to certain diacids or diols as "precursors" to a diol/diacid condensate does not require that such compounds actually be used in the preparation of the diol/diacid condensate; rather this terminology is used to designate compounds from which diol/diacid condensates could formally be derived.

A precursor diacid can be any dicarboxylic acid, e.g., straight chain, branched chain, or cyclic alkylene or alkenylene dicarboxylic acids (such as oxalic acid, malonic acid, succinic acid, pentane-, hexane-, and heptanedioic acids, cis or trans 1,2-cyclohexanedicarboxylic acid) wherein the alkylene or alkenylene moiety optionally contains carbonyl, oxy, thio, or catenary preferably fully substituted nitrogen. Also suitable are aromatic diacids such as phthalic acid, 1,4-benzenedicarboxylic acid, isophthalic acid, 2,3-furandicarboxylic acid, 1,2-benzenediacetic acid, and the like. The anhydrides corresponding to the above-noted diacids (such as succinic anhydride, diglycolic anhydride, and the like) are also suitable.

A precursor diol can be any dihydridic alcohol. Suitable precursor diols include straight chain, branched chain, or cyclic alkylene or alkenylene diols optionally containing carbonyl, oxy, thio, or catenary fully substituted nitrogen (e.g., ethylene or propylene glycol, 1,4-butanediol, 1,6-hexanediol, and the like), polyoxyalkylene diols (e.g., polyethylene glycol, polypropylene glycol, block copolymers comprising polyoxyethylene units and polyoxypropylene units), and the like.

A diol/diacid condensate unit can be designated by the general formula

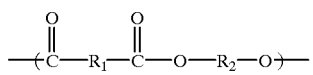

wherein $R_1$ designates an organic moiety that functions to link the carbonyl groups

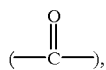

and $R_2$ is an organic moiety that links the oxy groups. In a chain of diol/diacid condensate units each $R_1$ and $R_2$ are independently selected. $R_1$ and $R_2$ are preferably straight chain, branched chain, or cyclic alkylene or alkenylene, preferably containing from two to about six carbon atoms. When $R_1$ or $R_2$ is alkylene or alkenylene it can also contain heteroatomic functional groups such as carbonyl, oxy, thio, or catenary preferably fully substituted nitrogen, preferably wherein the substituent is free of hydrogen-donor hydrogen bonding functional groups. $R_1$ and/or $R_2$ can also be arylene (e.g., 1,2-, 1,3-, or 1,4-phenylene) or arylene substituted by lower alkyl, lower alkoxy, or halogen. "Lower" as used herein designates straight chain or branched chain groups having from one to about four carbon atoms. $R_1$ and/or $R_2$ can also be a combination of such arylene and alkylene or alkenylene groups, such as 1,4-xylylene.

One skilled in the art can select units for inclusion in the chains of the compounds of the dispersing aid described above with due consideration of factors that affect the dispersing aid function or suitability for inhalation, such as possible ease of metabolism, solubility, crystallinity, structural homogeneity, molecular weight, degree of branching, relative amount of polar and non-polar portions of the chain, the particular propellant to be used in connection with the dispersing aid, and the particular drug to be formulated. For example, certain homopolymer chains or chains having excess aromatic content can be excessively crystalline and unsuitable for use with HFC propellants. The use of minor amounts (e.g., 10 to 40 mole percent) of "comonomers" can serve to render the material more amorphous. Likewise, excessive hydrogen bonding can interfere with dispersing aid function but is readily avoided by selecting appropriate chain components.

A product dispersing aid will contain a mixture of components of varying molecular weights. The term "chain length" as used herein (sometimes referred to as "n" in connection with the several formulae appearing herein) refers to the average chain length of the mixture. Generally chains contain a plurality of the above-described units. Chain length is generally less than 100, preferably between about 3 and about 70, and more preferably between about 3 and about 40, and most preferably between about 3 and about 12. Particularly preferred chain length will depend on certain of those factors discussed above. Relatively short chain lengths (e.g., from six to about twelve) are preferred inasmuch as these shorter chains could be expected to be more readily metabolized than materials having greater chain length. It is well known that polymers and/or oligomers contain a distribution of chain lengths. In those dispersing aids where excessive crystallinity is problematic it is often helpful to remove the higher molecular weight fraction from the dispersing aid composition.

A diol/diacid condensate chain can be terminated by terminal groups that are introduced, e.g., as a result of the method of synthesis discussed below. A chain can optionally be capped at one or both ends by a monovalent, divalent or polyvalent organic moiety (each valence of the capping group being independently bonded to a chain) that does not contain hydrogen atoms capable of hydrogen bonding. Such groups are well known and can be readily selected by those skilled in the art. Preferred monovalent organic moieties for capping the oxy terminus of the chain include organocarbonyl groups such as those of formula 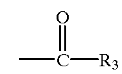 wherein $R_3$ is straight chain, branched chain, or cyclic alkyl optionally containing heteroatomic functional groups such as carbonyl, oxy, thio, or catenary nitrogen, preferably containing one to about eighteen carbon atoms, and more preferably containing one to about six carbon atoms, phenyl, or phenyl substituted by one or more lower alkyl, lower alkoxy, or halogen groups. A preferred capping group is acetyl.

The chain is also preferably bonded at one end or both ends to a moiety that contains an ionic group or a group that contains hydrogen atoms capable of hydrogen bonding. Such groups are well known and can be readily selected by those skilled in the art. Suitable ionic groups include quaternary ammonium groups, sulfonate salts, carboxylate salts, and the like. Hydrogen, when bonded to the heteroatom terminus of a chain, is capable of hydrogen bonding. Other suitable groups that contain hydrogen atoms capable of hydrogen bonding include acid functional groups, amides, carbamates, and groups such as amino, hydroxyl, thiol, aminoalkyl, alkylamino, hydroxyalkyl, hydroxyalkylamino, sugar residues, and the like. The suitability of any particular group for use in connection with a particular chain will of course be dependent upon the structure of the respective group and chain. Those skilled in the art can readily select suitable combinations with due consideration of factors known to affect functional group compatibility.

Suitable acid functional groups include carboxylic acid, which is an inherent feature of the dispersing aids prepared according to step (i) or step (ii) of the Reaction Scheme discussed in detail below. Other preferred moieties that contain acid functional groups include α-amino acid residues or esters thereof. In one such embodiment the amino group of the α-amino acid is bonded to a carbonyl terminus of the chain. In such embodiments preferred a-amino acid residues include those of the formula 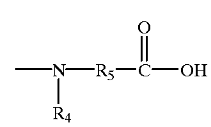 wherein $R_4$ is hydrogen and $R_5$ is straight chain, branched chain, or cyclic alkylene containing one catenary carbon atom and a total of one to about 12 carbon atoms, optionally substituted by one or more of lower alkoxy, lower alkylthio, carboxy, mercapto, hydroxy, phenyl, hydroxyphenyl, indolyl, guanidinyl, carbamido (i.e., $-NHC(O)NH_2$), imidazolyl, or acylamino (i.e., $-C(O)NH_2$), or wherein $R_4$ and $R_5$ together form a straight chain butane-1,1,4-triyl group optionally substituted by hydroxy. In embodiments wherein the amino acid residue contains a nucleophilic group such as hydroxy or mercapto, the amino group can be blocked, e.g., by an acetyl group, and the terminus of a chain can be bonded to the amino acid residue via the nucleophilic —S— or —O— atom of the amino acid.

In another embodiment the a-amino acid residue is bonded to the heteroatom terminus (e.g., to an —O—, —S—, or —NR'— group) of the chain and is of the formula

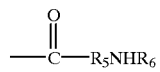

wherein $R_5$ is as defined above and $R_6$ is hydrogen or a blocking group such as organocarbonyl (e.g., acetyl) as defined above.

Most preferred amino acid residues are those that are derived from endogenous amino acids or esters thereof such as glycine, alanine, valine, leucine, isoleucine, serine, threonine, phenylalanine, tyrosine, tryptophan, cysteine, methionine, aspartic acid, glutamic acid, asparagine, glutamine, lysine, hydroxylysine, arginine, citrulline, histidine, proline, and hydroxyproline. Taurine, a β-amino sulfonic acid, is also suitable.

Particular preferred embodiments of the dispersing aid include those wherein the chain comprises units derived from a diol selected from ethylene glycol, propylene glycol, and 1,3-propanediol and a diacid selected from adipic acid, diglycolic acid, and succinic acid. A particular preferred poly(ethylene adipate) has a number average molecular weight of about 3900 and a weight average molecular weight of about 9600. Likewise a particular preferred poly (ethylene succinate) has a number average molecular weight of about 2800 and a weight average molecular weight of about 7300.

It is preferred (but as described below in connection with preparation of a formulation of the invention, not necessary) that the dispersing aid is soluble in the propellant contained in the formulation, e.g., in a propellant comprising a hydrofluorocarbon such as HFC-134a (1,1,1,2-tetrafluoroethane) or HFC-227 (1,1,1,2,3,3,3-heptafluoropropane), in an amount effective to stabilize a suspension aerosol formulation. The amount that constitutes such an effective amount will be dependent upon certain factors, including the structure of the particular dispersing aid, the particular propellant, the particular drug in the formulation, and the physical form of the drug (e.g., the particle size of the drug). Such effective amounts can be readily determined by those skilled in the art with due consideration of the factors discussed above.

A medicinal aerosol formulation of the invention comprises a dispersing aid as described above. An aerosol formulation preferably comprises the dispersing aid in an amount effective to stabilize the formulation relative to an identical formulation not containing the dispersing aid such that the drug does not settle, cream, or flocculate after agitation so quickly as to prevent reproducible dosing of the drug. Reproducible dosing can be achieved if the formulation retains a substantially uniform drug concentration for about two to three seconds after agitation.

The particular amount that constitutes an effective amount of dispersing aid is dependent upon the particular dispersing aid, the particular propellant, and on the particular drug and propellant used in the formulation. It is therefore not practical to enumerate specific effective amounts for use with specific formulations of the invention, but such amounts can readily be determined by those skilled in the art with due consideration of the factors set forth above. Generally, however, the dispersing aid can be present in a formulation in an amount of about 0.001 to about 1 part by weight, more preferably about 0.01 to about 0.25 parts by weight, based on 100 parts by weight of the propellant.

The formulations of the invention contain a drug in a therapeutically effective amount, that is, an amount such that the drug can be administered as an aerosol (e.g., topically or by oral or nasal inhalation) and cause its desired therapeutic effect with one dose, or less preferably several doses, from a conventional valve, e.g., a metered dose valve. "Amount" as used herein refers to quantity or to concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount will be from about 0.02 to about 2 parts by weight based on 100 parts by weight of the propellant.

Particularly in formulations of the invention intended for inhalation into the lungs, the drug is preferably micronized, i.e., a therapeutically effective fraction of the particles (e.g., about 90 percent or more) have a diameter of less than about 10 microns, in order to assure that the particles can be inhaled into the respiratory tract and/or lungs.

Suitable drugs for use in a formulation of the invention include any drug suitable for administration by inhalation. Therapeutic categories include antiallergics, analgesics, bronchodilators, antihistamines, antitussives, anginal preparations, antibiotics, antiinflammatories, peptides, proteins, and steroids. Particular suitable drugs include albuterol, atropine, beclomethasone, budesonide, cromolyn, epinephrine, ephedrine, fentanyl, flunisolide, formoterol, ipratropium bromide, isoproterenol, pirbuterol, prednisolone, salmeterol, and pharmaceutically acceptable salts and solvates thereof. Particularly preferred drugs include pirbuterol acetate and albuterol sulfate.

An aerosol formulation of the invention also comprises a propellant. Suitable propellants include conventional chlorofluorocarbon (CFC) propellants such as mixtures of propellants 11, 12, and 114. Non-CFC propellants, particularly 1,1,1,2-tetrafluoroethane (propellant 134a, HFC-134a), 1,1,1,2,3,3,3-heptafluoropropane (propellant 227, HFC-227), or mixtures thereof, are preferred. The propellant is preferably present in an amount sufficient to propel a plurality of doses of drug from an aerosol canister. Further components such as conventional lubricants or surfactants, cosolvents (e.g., ethanol) and the like can also be present in a formulation of the invention in suitable amounts readily determined by those skilled in the art.

Certain preferred dispersing aids for use in the formulations of the invention can be prepared as set forth in the Reaction Scheme below, wherein $R_1$, $R_2$, and $R_3$ are as defined above. Those skilled in the art will recognize that the general description given below is applicable to many dispersing aids that can be used in the formulations of the invention, whether or not the dispersing aids are within the ambit of the particular preferred formulas used in the Reaction Scheme.

Reaction Scheme

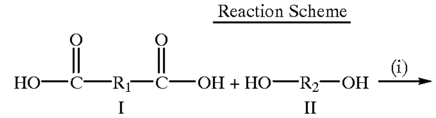

I II

-continued

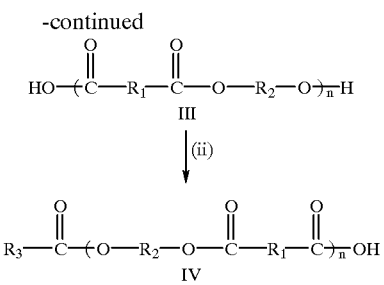

Step (i) of the Reaction Scheme involves condensing a dicarboxylic acid of Formula I with a diol of Formula II. The condensation can be carried out under conventional reaction conditions such as by heating the diacid and the diol optionally in an aprotic solvent, and preferably at a temperature sufficient to remove by distillation the water produced by the reaction (e.g., as part of an azeotropic mixture with the solvent). The product will comprise a compound having a chain represented by "n" repeating units of the parenthetical portion of Formula III. Chain length can be controlled by controlling the stoichiometry of the reaction or by using a monofunctional chain terminating reagent such as a monohydridic alcohol or acid.

A compound of Formula III can be used as a dispersing aid without further elaboration. In order to prepare certain preferred embodiments, however, an additional reaction can be carried out as described below.

In step (ii) of the Reaction Scheme a compound of Formula III can be capped at the oxy terminus by reacting with a compound containing an activated acyl group, e.g., an acid anhydride such as acetic anhydride or an acid chloride to afford a capped product of Formula IV. A product of Formula IV can be used as a dispersing aid without further elaboration.

In order to incorporate an amino acid residue into the compounds of a dispersing aid, the capped product, which still possesses a carboxylic acid group, can be converted by activating the carboxylic acid and reacting with an amino acid. The carboxylic acid is activated (e.g., converted to the corresponding acid halide) by general methods well known to those skilled in the art, such as by reacting with a carboxy activating reagent such as ethylchloroformate or a conventional chlorinating agent such as oxalyl chloride, $POCl_3$, $SOCl_2$, or the like. The amino acid group can then be incorporated by reacting the acid halide (or an analogous activated carboxy compound) with the amino acid.

Other variants of the Reaction Scheme can be readily devised in order to prepare dispersing aids other than those illustrated. For example, the carboxy end of the compound of Formula III can be capped via esterification and/or the oxy end of the resulting compound can be reacted with a cyclic anhydride to incorporate an acid group.

An alternative method of preparing preferred embodiments involves reacting an anhydride with the diol.

Molecular weight distribution of a product dispersing aid can be adjusted and optimized by using methods well known to those skilled in the art. Generally the dispersing aid can be fractionated by distillation or precipitation in order to provide the desired distribution.

Generally the formulations of the invention can be prepared by combining (i) the drug in an amount sufficient to provide a plurality of therapeutically effective doses; (ii) the dispersing aid; (iii) the propellant in an amount sufficient to propel a plurality of doses from an aerosol canister; and (iv) any further optional components; and dispersing the components. The components can be dispersed using a conventional mixer or homogenizer, by shaking, or by ultrasonic energy. Bulk formulation can be transferred to smaller individual aerosol vials by using valve to valve transfer methods or by using conventional cold-fill methods. It is not required that a dispersing aid used in a suspension aerosol formulation be soluble in the propellant. Those that are not can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular surfactants and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.), or an EPDM rubber such as those disclosed in commonly assigned copending application 08/092,001. Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, e.g., those of aluminum, glass, stainless steel, or polyethylene terephthalate, can be used to contain a formulation of the invention.

The formulations of the invention can be delivered to the respiratory tract and/or the lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, or diabetes, or they can be delivered via topical (e.g., buccal) administration in order to treat, e.g., angina or local infection.

The following Examples are provided to illustrate the invention. All parts and percentages are by weight unless otherwise indicated.

In the preparations of the dispersing aids set forth below the structure was determined by nuclear magnetic resonance spectroscopy. The number-average relative molecular mass $M_N$ and the weight-average relative molecular mass $M_W$ were determined using gel permeation chromatography. The instrument used was a Hewlett-Packard 1090-LUSI equipped with a UV detector set at 254 nm and a refractive index detector (HP 1037A). The column set comprised 500 Angstrom columns from Jordi Associates. The samples were dissolved in tetrahydrofuran at an approximate concentration of 25 mg solids/10 mL and pressure filtered through a 0.2 micron alpha cellulose filter. An injection size of 150 $\mu$L was handled by a Hewlett-Packard 9816 computer with software supplied by Nelson Analytical. Molecular weight data are based on a calibration with polystyrene standards.

Neutralization titrations for acid content were performed by dissolution of the sample in tetrahydrofuran followed by addition of ultrapure water. Titration with a methanolic potassium hydroxide solution was performed using potentiotitrimetry. A potentiograph equipped with a combination glass pH electrode was employed for automated dosing and plotting of titration curves.

Dispersing Aid A

Ethylene glycol (11.95 g, 0.178 moles), diglycolic anhydride (20.02 g, 0.172 moles), glacial acetic acid (2.07 g, 0.0345 moles), toluene (25 mL) and antimony III oxide (1 mg) were placed in a 50 mL reaction flask equipped with a Dean-Stark trap. The reaction mixture was heated at reflux under nitrogen for 48 hours in order to azeotropically remove water. The toluene was then removed by distillation and acetic anhydride (30 g) was added. The mixture was heated at 80° C. under nitrogen for 16 hours. Excess acetic anhydride and acetic acid were removed by vacuum distillation on a rotary evaporator. The resulting crude product was dissolved in 30 mL of tetrahydrofuran/water (85/15;v/v) and stirred at 50° C. for 20 minutes. The bulk of the solvents were then removed by vacuum distillation on a rotary evaporator and the residual volatiles were removed under high vacuum at 120° C. on a Kugelrohr apparatus. The resulting product was identified by proton NMR as acetyl oligo(ethylene diglycolate). $M_N$=1200; $M_W$=1650; and meq Acid/gram=0.68.

Dispersing Aid B

Propylene glycol (13.11 g, 0.172 moles), diglycolic anhydride (20.13 g, 0.173 moles), glacial acetic acid (2.07 g, 0.0345 moles), toluene (25 mL) and antimony III oxide (1 mg) were placed in a 50 mL reaction flask equipped with a Dean-Stark trap. The reaction mixture was heated at reflux under nitrogen for 48 hours in order to azeotropically remove water. The toluene was then removed by distillation and acetic anhydride (30 g) was added. The mixture was heated at 80° C. under nitrogen for 16 hours. Excess acetic anhydride and acetic acid were removed by vacuum distillation on a rotary evaporator. The resulting crude product was dissolved in 30 mL of tetrahydrofuran/water (85/15;v/v) and stirred at 50° C. for 20 minutes. The bulk of the solvents were then removed by vacuum distillation on a rotary evaporator and the residual volatiles were removed under high vacuum at 120° C. on a Kugelrohr apparatus. The resulting product was identified by proton NMR as acetyl oligo(propylene diglycolate). $M_N$=1360; $M_W$=2110; and meq Acid/gram=0.88.

Dispersing Aid C 1,3 Propanediol (13.11 g, 0.175 moles), diglycolic anhydride (20.09 g, 0.178 moles), glacial acetic acid (2.07 g, 0.0345 moles), toluene (25 mL) and antimony III oxide (1 mg) were placed in a 50 mL reaction flask equipped with a Dean-Stark trap. The reaction mixture was heated at reflux under nitrogen for 48 hours in order to azeotropically remove water. The toluene was then removed by distillation and acetic anhydride (30 g) was added. The mixture was heated at 80° C. under nitrogen for 16 hours. Excess acetic anhydride and acetic acid were removed by vacuum distillation on a rotary evaporator. The resulting crude product was dissolved in 30 mL of tetrahydrofuran/water (85/15;v/v) and stirred at 50° C. for 20 minutes. The bulk of the solvents were then removed by vacuum distillation on a rotary evaporator and the residual volatiles were removed under high vacuum at 120° C. on a Kugelrohr apparatus. The resulting product was identified by proton NMR as acetyl oligo(trimethylene diglycolate). $M_N$=1870; $M_W$=3110; and meq Acid/gram=0.72.

Dispersing Aid D

Ethylene glycol (13.41 g, 0.200 moles), succinic anhydride (20.05 g, 0.200 moles), glacial acetic acid (2.4 g, 0.040 moles), toluene (25 mL) and antimony III oxide (1 mg) were placed in a 50 mL reaction flask equipped with a Dean-Stark trap. The reaction mixture was heated at reflux under nitrogen for 48 hours in order to azeotropically remove water. The toluene was then removed by distillation and acetic anhydride (30 g) was added. The mixture was heated at 80° C. under nitrogen for 16 hours. Excess acetic anhydride and acetic acid were removed by vacuum distillation on a rotary evaporator. The resulting crude product was dissolved in 30 mL of tetrahydrofuran/water (85/15;v/v) and stirred at 50° C. for 20 minutes. The bulk of the solvents were then removed by vacuum distillation on a rotary evaporator and the residual volatiles were removed under high vacuum at 120° C. on a Kugelrohr apparatus. The resulting product was identified by proton NMR as acetyl oligo(ethylene succinate). $M_N$=940; $M_W$=1320; and meq Acid/gram=1.02.

Dispersing Aid E

Propylene glycol (15.31 g, 0.201 moles), succinic anhydride (20.00 g, 0.199 moles), glacial acetic acid (2.4 g, 0.0399 moles), toluene (25 mL) and antimony III oxide (1 mg) were placed in a 50 mL reaction flask equipped with a Dean-Stark trap. The reaction mixture was heated at reflux under nitrogen for 48 hours in order to azeotropically remove water. The toluene was then removed by distillation and acetic anhydride (30 g) was added. The mixture was heated at 80° C. under nitrogen for 16 hours. Excess acetic anhydride and acetic acid were removed by vacuum distillation on a rotary evaporator. The resulting crude product was dissolved in 30 mL of tetrahydrofuran/water (85/15;v/v) and stirred at 50° C. for 20 minutes. The bulk of the solvents were then removed by vacuum distillation on a rotary evaporator and the residual volatiles were removed under high vacuum at 120° C. on a Kugelrohr apparatus. The resulting product was identified by proton NMR as acetyl oligo(propylene succinate). $M_N$=730; $M_W$=980; and meq Acid/gram=1.47.

Dispersing Aid F 1,3 Propanediol (15.21 g, 0.199 moles), succinic anhydride (20.08 g, 0.201 moles), glacial acetic acid (2.40 g, 0.040 moles), toluene (25 mL) and antimony III oxide (1 mg) were placed in a 50 mL reaction flask equipped with a Dean-Stark trap. The reaction mixture was heated at reflux under nitrogen for 48 hours in order to azeotropically remove water. The toluene was then removed by distillation and acetic anhydride (30 g) was added. The mixture was heated at 80° C. under nitrogen for 16 hours. Excess acetic anhydride and acetic acid were removed by vacuum distillation on a rotary evaporator. The resulting crude product was dissolved in 30 mL of tetrahydrofuran/water (85/15;v/v) and stirred at 50° C. for 20 minutes. The bulk of the solvents were then removed by vacuum distillation on a rotary evaporator and the residual volatiles were removed under high vacuum at 120° C. on a Kugelrohr apparatus. The resulting product was identified by proton NMR as acetyl oligo(trimethylene succinate). $M_N$=1180; $M_W$=1840; and meq Acid/gram=1.14.

Dispersing Aid G

A poly(ethylene adipate) with $M_N$=3885 and $M_W$9564 was obtained from a commercial source (#147 from Scientific Polymer Products, Ontario, N.Y.).

Dispersing Aid H

A poly(ethylene succinate) with $M_N$=2837 and $M_W$=7321 was obtained from a commercial source (#150 from Scientific Polymer Products, Ontario, N.Y.).

Suspension aerosol formulations were prepared using the following general method:

Dispersing aid (about 40 mg) was placed in a 4 oz (120 mL) glass aerosol vial. A continuous valve was crimped onto the vial, the vial was pressure filled with about 80 g of propellant, either HFC 134a or HFC 227, then the vial was sonicated for 5 minutes to provide a stock mixture containing 0.05% by weight of dispersing aid. Micronized drug (about 30 mg) and glass beads (5 mL) were placed into a 15 mL glass aerosol vial. The vial was sealed with a continuous valve then pressure filled with the stock mixture. The vial was then shaken on a paint shaker for 10 minutes to provide an aerosol suspension formulation. The resulting suspension was stored at room temperature then shaken by hand and rated on a scale of 1 to 5. A rating of 1 indicated that agglomerates formed during shaking. A rating of 2 indicated that the suspension began flocculating immediately after shaking had ceased. A rating of 3 indicated that flocculation began 1 to 5 seconds after shaking, long enough to allow reproducible dosing of the drug. A rating of 4 indicated that flocculation began 5 to 10 seconds after shaking. A rating of 5 indicated that flocculation did not begin until at least 10 seconds after shaking had ceased. The table below shows the formulations that were prepared and the rating that each received. In all formulations the dispersing aid was present at 0.05% by weight; but, with the exception of Dispersing Aid E, none of the dispersing aids tested were completely dissolved when mixed with either HFC 134a or HFC 227 at 0.5% by weight. The drug was present at 0.3% by weight except as indicated. The absence of an entry indicates that the formulation was not prepared.

TABLE 1

| | Dispersing | Pirbuterol Acetate | | Albuterol Sulfate | | Triamcinolone Acetonide | | Pirbuterol Hydrochloride | | Albuterol Free base | |
|---|---|---|---|---|---|---|---|---|---|---|---|
| Example | Aid | 134a | 227 | 134a | 227 | 134a | 227 | 134a | 227 | 134a | 227 |
| 1 | A | 2 | 3 | 3 | 3 | 2 | 2 | | | | |
| 2 | B | 2 | 3 | 2 | 3 | 2 | 2 | | | | |
| 3 | C | 2 | 3 | 2 | 3 | 2 | 2 | | | | |
| 4 | D | 2 | 3 | 2 | 3 | 2 | 2 | | | | |
| 5 | E | 2 | 3 | 2 | 3 | 2 | 2 | | | | |
| 6 | F | 2 | 3 | 2 | 2 | 2 | 2 | | | | |
| 7 | G | 3[1] | 3[1] | 2[1] | 3[1] | 2 | 2 | 2[1] | 2[1] | 2[1] | 2[1] |
| 8 | H | 3[1] | 3[1] | 3[1] | 3[1] | 2 | 2 | 2[1] | 2[1] | 2[1] | 2[1] |

[1]Drug was present in these formulations at 0.5% by weight.

The results in the TABLE show that the dispersing aids afford formulations of the invention that are substantially readily redispersible and upon redispersion do not flocculate, settle, or cream so quickly as to prevent reproducible dosing of the drug.

The claimed invention is:

1. A medicinal aerosol formulation, comprising:

(i) a dispersing aid comprising a compound comprising a chain of diol/diacid condensate units;

(ii) a propellant; and (iii) a therapeutically effective amount of a particulate drug;

wherein the formulation is readily redispersible and when redispersed does not flocculate, settle, or cream so quickly as to prevent reproducible dosing of the drug.

2. A formulation according to claim 1, wherein the dispersing aid comprises a compound comprising a plurality of units of the formula 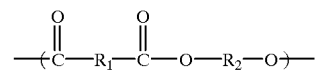 wherein each $R_1$ is an independently selected organic moiety that links the carbonyl groups and each $R_2$ is an independently selected organic moiety that links the oxy groups.

3. A formulation according to claim 2, comprising less than about 100 of said units.

4. A formulation according to claim 2, comprising between about 3 and about 70 of said units.

5. A formulation according to claim 2, comprising between about 3 and about 12 of said units.

6. A formulation according to claim 2, wherein $R_1$ and $R_2$ are independently selected from the group consisting of straight chain, branched chain, or cyclic alkylene or alkenylene optionally containing carbonyl, oxy, thio, or catenary nitrogen; arylene; arylene substituted by lower alkyl, lower alkoxy, or halogen; or a combination of such alkylene, alkenylene, and arylene groups.

7. A formulation according to claim 6, wherein $R_1$ and $R_2$ are independently selected from the group consisting of straight chain, branched chain, or cyclic alkylene or alkenylene containing two to about 6 carbon atoms, optionally containing carbonyl, oxy, thio, or catenary fully substituted nitrogen; arylene; arylene substituted by lower alkyl, lower alkoxy, or halogen; or a combination of such alkylene, alkenylene, and arylene groups.

8. A formulation according to claim 6, wherein $R_1$ and $R_2$ are independently selected from the group consisting of straight chain, branched chain, or cyclic alkylene or alkenylene containing one to about 6 carbon atoms, optionally containing carbonyl, oxy, thio, or catenary fully substituted nitrogen wherein the substituent is free of hydrogen-donor hydrogen bonding functional groups; arylene; arylene substituted by lower alkyl, lower alkoxy, or halogen; or a combination of such alkylene, alkenylene, and arylene groups.

9. A formulation according to claim 2, wherein $R_1$ and $R_2$ are ethylene.

10. A formulation according to claim 2, wherein $R_1$ is tetramethylene and $R_2$ is ethylene.

11. A formulation according to claim 1, wherein the dispersing aid is present in an amount of about 0.001 to about 1 part by weight based on 100 parts by weight of the propellant.

12. A formulation according to claim 1, wherein the propellant comprises 1,1,1,2-tetrafluoroethane, 1,1,1,2,3,3,3-heptafluoropropane, or a mixture thereof.

13. A formulation according to claim 1, wherein the drug is selected from the group consisting of albuterol, atropine, beclomethasone, budesonide, cromolyn, epinephrine, ephedrine, fentanyl, flunisolide, formoterol, ipratropium bromide, isoproterenol, pirbuterol, prednisolone, salmeterol, and pharmaceutically acceptable salts and solvates thereof.

14. A formulation according to claim 1, wherein the drug is pirbuterol acetate or albuterol sulfate.

15. A method of preparing a medicinal aerosol formulation according to claim 1, comprising the steps of:
   (a) combining (i) the drug in an amount sufficient to provide a plurality of therapeutically effective doses; (ii) the dispersing aid; and (iii) the propellant in an amount sufficient to propel a plurality of doses from an aerosol canister; and
   (b) dispersing components (i)–(iii).

16. A method of treating in an animal a condition capable of treatment by oral or nasal inhalation, comprising the steps of: (i) providing a formulation according to claim 1; and (ii) administering said formulation to said animal by oral or nasal inhalation.

17. A formulation according to claim 1 in an aerosol canister equipped with a metered dose valve.

18. A formulation according to claim 1 wherein the chain is a straight chain.

19. A formulation according to claim 2, wherein $R_1$ is selected from the group consisting of ethylene and —$CH_2$—O—$CH_2$— and $R_2$ is selected from the group consisting of ethylene, propylene and trimethylene.

20. A formulation according to claim 1, wherein the chain is capped on at least one end by a group that contains no hydrogen atoms capable of hydrogen bonding.

21. A formulation according to claim 20, wherein said group comprises an organocarbonyl group, an alkyl group, or an alkoxy group.

22. A formulation according to claim 21, wherein the organocarbonyl group is alkylcarbonyl.

23. A formulation according to claim 1, wherein the chain is bonded on at least one end to a moiety comprising an ionic group or a group that contains hydrogen atoms capable of hydrogen bonding.

24. A method of stabilizing a suspension aerosol formulation comprising a propellant and particulate drug, comprising the step of incorporating into said formulation a dispersing aid comprising a compound comprising a chain of diol/diacid condensate units in an amount effective to prevent settling, creaming, or flocculation of the formulation for a time sufficient to allow reproducible dosing of